(12) United States Patent
Sotoyama et al.

(10) Patent No.: US 7,083,867 B2
(45) Date of Patent: Aug. 1, 2006

(54) PEROPYRENE COMPOUND, ORGANIC ELECTROLUMINESCENT ELEMENT AND ORGANIC ELECTROLUMINESCENT DISPLAY

(75) Inventors: Wataru Sotoyama, Kawasaki (JP); Tasuku Sato, Kawasaki (JP); Hiroyuki Sato, Kawasaki (JP); Azuma Matsuura, Kawasaki (JP); Norio Sawatari, Kawasaki (JP); Toshiaki Narusawa, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 11/126,325

(22) Filed: May 11, 2005

(65) Prior Publication Data

US 2005/0202281 A1    Sep. 15, 2005

Related U.S. Application Data

(63) Continuation of application No. PCT/JP03/14137, filed on Nov. 6, 2003.

(30) Foreign Application Priority Data

Nov. 14, 2002  (JP) .............................. 2002-330533

(51) Int. Cl.
  *H01L 51/54*   (2006.01)
  *H05B 33/14*   (2006.01)
  *C07C 211/61*  (2006.01)
  *C09K 11/06*   (2006.01)

(52) U.S. Cl. ...................... 428/690; 428/917; 313/504; 313/506; 257/88; 257/E51.049; 257/E51.051; 564/426; 564/429; 564/434

(58) Field of Classification Search ...................... None
See application file for complete search history.

(56) References Cited

FOREIGN PATENT DOCUMENTS

| EP | 0 034 274 A2 | 8/1981 |
|---|---|---|
| JP | 05-179237 | 7/1993 |
| JP | 2000-58261 | 2/2000 |
| JP | 2000-231987 | 8/2000 |

OTHER PUBLICATIONS

C.W. Tang et al.; "Organic electroluminescent diodes"; Appl. Phys. Letter 51, (12); Sep. 21, 1987, pp. 913-915; 1987 American Institute of Physics.
C.W. Tang et al.; "Electroluminescence of doped organic thin films"; J. Appl. Phys. 65 (9), May 1, 1989, pp. 3610-3616; 1989 American Institute of Physics.

*Primary Examiner*—Marie Yamnitzky
(74) *Attorney, Agent, or Firm*—Westerman, Hattori, Daniels & Adrian, LLP.

(57) ABSTRACT

An organic electroluminescent element contains a positive electrode, a negative electrode, and a thin organic layer arranged between the positive electrode and the negative electrode, wherein the thin organic layer comprises, as a luminescent material, a peropyrene compound represented by following Structural Formuala (1):

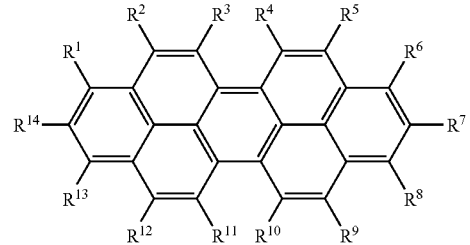

Structural Formula (1)

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent hydrogen atom or a substituent:

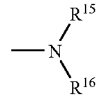

Structural Formula (2)

wherein $R^{15}$ and $R^{16}$ may be the same as or different from each other and each represent one of hydrogen atom, an alkyl group and an aryl group, where $R^{15}$ and $R^{16}$ may be bound to each other directly or indirectly.

23 Claims, 6 Drawing Sheets

PEROPYRENE COMPOUND, ORGANIC ELECTROLUMINESCENT ELEMENT AND ORGANIC ELECTROLUMINESCENT DISPLAY

CROSS-REFERENCE TO RELATED APPLICATIONS

This is a continuation of Application PCT/JP03/014137, filed on Nov. 6, 2003.

BACKGROUND OF THE INVENTION

1. Field of the Invention

The present invention relates to a peropyrene compound suitable as a luminescent material for an organic electroluminescent element, an organic electroluminescent element using the peropyrene compound, and an organic electroluminescent display using the organic electroluminescent element.

2. Description of the Related Art

Organic electroluminescent elements have features such as self-luminescence and high-speed response and their application for flat panel displays are expected. In particular, two-layer (multilayered) organic electroluminescent elements receive attention as large-area luminescent elements capable of emitting light at low voltages of 10 V or less. Such multilayered organic electroluminescent elements each comprise a hole-transporting organic thin film (hole-transporting layer) and an electron-transporting organic thin film (electron-transporting layer) and have been reported typically in C. W. Tang and S. A. VanSlyke, Applied Physics Letters vol. 51, 913 (1987). Such multilayered organic electroluminescent elements basically have a basic configuration of positive electrode/hole-transporting layer/light-emitting layer/electron-transporting layer/negative electrode, in which the hole-transporting layer or the electron-transporting layer may also serve as the light-emitting layer as in the two-layer organic electroluminescent element.

The application of organic electroluminescent elements for a full-color display have been expected. In the full-color display, pixels showing three primary colors, i.e., blue (B), green (G) and red (R), must be arranged on a panel. Proposed methods for arranging the pixels are (a) a method of arranging three different organic electroluminescent elements emitting blue (B), green (G) and red (R) light, respectively; (b) a method of separating white light (color mixture of blue (B), green (G) and red (R) light) emitted from a white-light-emitting organic electroluminescent element into the three primary colors using a color filter; and (c) a method of converting blue light from a blue-light-emitting organic electroluminescent element into green (G) light and red (R) light with the use of a color conversion layer utilizing fluorescence emission.

A technique for yielding an organic electroluminescent element having a high emission efficiency is proposed in, for example, C. W. Tang, S. A. VanSlyke, and C. H. Chen, Journal of Applied Physics vol. 65, 3610 (1989). According to this technique, a host material serving as a main material is doped with a small amount of a dye molecule capable of highly emitting fluorescence as a guest material to form a light-emitting layer exhibiting a high emission efficiency.

These conventional organic electroluminescent elements, in particular those for emitting red light, however, are still insufficient in emission efficiency (for example, Japanese Patent Application Laid-Open (JP-A) No. 2000-231987) and demands have been made to develop novel and high-performance organic electroluminescent elements.

Accordingly, an object of the present invention is to solve the problems in conventional technologies and to provide a peropyrene compound suitable as a red-light emitting material in an organic electroluminescent element and to provide an organic electroluminescent element which is excellent typically in emission efficiency, emission luminance and color purity of red light. Another object of the present invention is to provide a high-performance organic electroluminescent display using the organic electroluminescent element.

After intensive investigations to achieve the above objects, the present inventors have obtained the following findings. Specifically, they have found that a specific peropyrene compound is suitable as a red-light emitting material in an organic electroluminescent element, and that an organic electroluminescent element and an organic electroluminescent display each using the peropyrene compound as a luminescent material are excellent typically in emission efficiency, emission luminance and color purity of red light and exhibit higher performance than conventional equivalents.

SUMMARY OF THE INVENTION

An organic electroluminescent element according to the present invention includes a positive electrode, a negative electrode and a thin organic layer arranged between the positive electrode and the negative electrode, wherein the thin organic layer contains, as a luminescent material, a peropyrene compound represented by following Structural Formula (1):

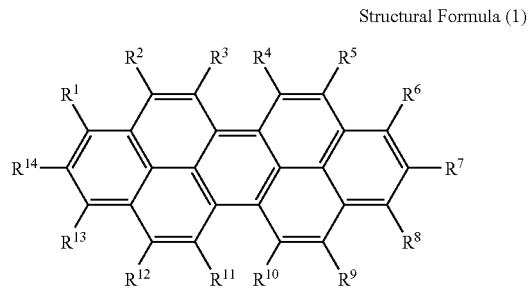

Structural Formula (1)

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent hydrogen atom or a substituent:

Structural Formula (2)

wherein $R^{15}$ and $R^{16}$ may be the same as or different from each other and each represent one of hydrogen atom, an alkyl group and an aryl group, where $R^{15}$ and $R^{16}$ may be bound to each other directly or indirectly.

The organic electroluminescent element of the present invention contains the specific peropyrene compound as a luminescent material and is excellent typically in emission efficiency, emission luminance and color purity of red light.

A peropyrene compound according to the present invention is represented by following Structural Formula (1):

Structural Formula (1)

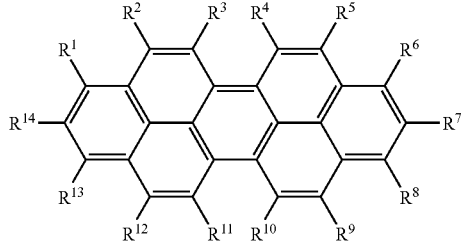

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent hydrogen atom or a substituent:

Structural Formula (2)

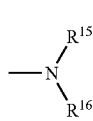

wherein $R^{15}$ and $R^{16}$ may be the same as or different from each other and each represent one of hydrogen atom, an alkyl group and an aryl group, where $R^{15}$ and $R^{16}$ may be bound to each other directly or indirectly.

The peropyrene compound of the present invention serves to emit red light typically with excellent emission efficiency, emission luminance and color purity when used as a luminescent material in an organic electroluminescent element.

An organic electroluminescent display according to the present invention uses the organic electroluminescent element of the present invention. The organic electroluminescent display of the present invention comprises the organic electroluminescent element of the present invention and is thereby excellent typically in emission efficiency, emission luminance and color purity of red light.

DESCRIPTION OF THE PREFERRED EMBODIMENTS

<Peropyrene Compound>

Figure 1:
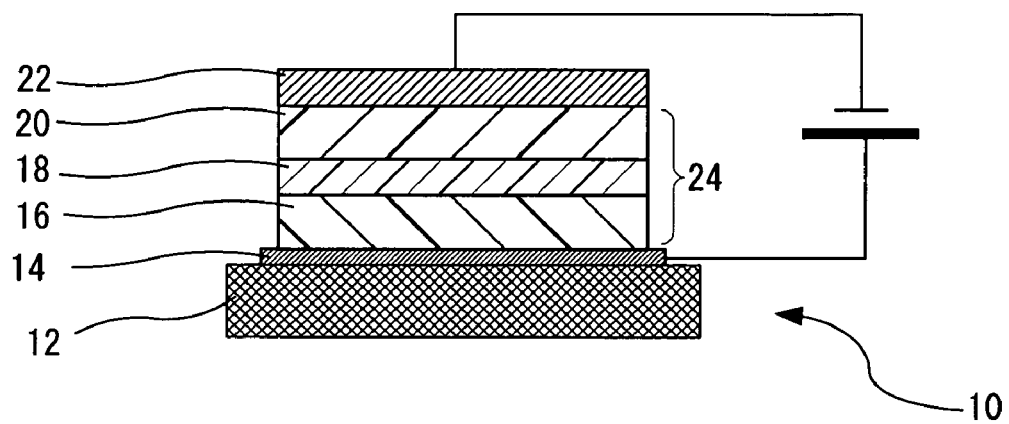
FIG. 1 is a schematic diagram illustrating an example of layer configuration of the organic electroluminescent element according to the present invention.

The peropyrene compound of the present invention is represented by following Structural Formula (1):

Structural Formula (1)

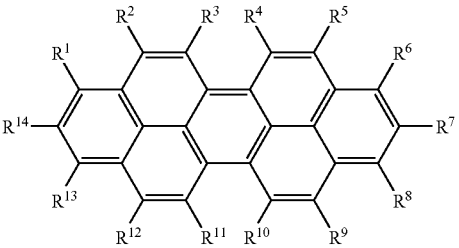

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent a hydrogen atom or a substituent mentioned below:

Structural Formula (2)

wherein $R^{15}$ and $R^{16}$ may be the same as or different from each other and each represent one of hydrogen atom, an alkyl group and an aryl group. The alkyl group or the aryl group may be substituted with a substituent mentioned below.

The substituent can be any suitable one selected according to the purpose and includes, for example, an alkyl group and an aryl group, and each of these substituents may further be substituted with one or more substituents. The substituents just mentioned above are not specifically limited and can be appropriately selected from among known substituents.

The alkyl group can be any suitable one selected according to the purpose and includes, for example, linear, branched-chain or cyclic alkyl groups each having one to ten carbon atoms. Suitable examples thereof are methyl, ethyl, propyl, isopropyl, butyl, isobutyl, t-butyl, pentyl, isopentyl, hexyl, isohexyl, heptyl, isoheptyl, octyl, isooctyl, nonyl, isononyl, decyl, isodecyl, cyclopentyl, cyclobutyl, cyclopentyl, cyclohexyl, cycloheptyl, cyclooctyl, cyclononyl and cyclodecyl.

The aryl group can be any suitable one selected according to the purpose and includes, for example, a group having a monocyclic aromatic ring; a group having combined four or less aromatic rings; and a group having fused five or less aromatic rings and containing a total of fifty or less atoms including carbon, oxygen, nitrogen and sulfur atoms.

The group having a monocyclic aromatic ring can be any suitable one selected according to the purpose and includes, for example, phenyl, tolyl, xylyl, cumenyl, styryl, mesityl, cinnamyl, phenethyl and benzhydryl. Each of these may further be substituted with one or more substituents.

The group having combined four or less aromatic rings can be any suitable one selected according to the purpose and includes, for example, naphthyl, anthryl, phenanthryl, indenyl, azulenyl and benzanthracenyl. Each of these may further be substituted with one or more substituents.

The group having fused five or less aromatic rings and containing a total of fifty or less atoms including carbon, oxygen, nitrogen and sulfur atoms can be any suitable one selected according to the purpose and includes, for example, pyrrolyl, furyl, thienyl, pyridyl, quinolyl, isoquinolyl, imidazoyl, pyridinyl, pyrrolopyridinyl, thiazoyl, pyrimidinyl, thiophenyl, indolyl, quinolinyl, purinyl and adenyl. Each of these may be substituted with one or more substituents.

$R^{15}$ and $R^{16}$ may be bound to each other directly or indirectly. In the latter case, they may be bound to each other with the interposition of at least one atom selected from boron, carbon, nitrogen, oxygen, silicon, phosphorus and sulfur atoms.

In the present invention, $R^1$, $R^6$, $R^8$ and $R^{13}$ (the groups represented by Structural Formula (2)) in Structural Formula (1) are each preferably a group represented by one of following Structural Formulae (3), (4) and (5).

The peropyrene compound is 1,3,8,10-tetrakis(N,N-diphenylamino)peropyrene when $R^1$, $R^6$, $R^8$ and $R^{13}$ (the groups represented by Structural Formula (2)) in Structural Formula (1) are each the group represented by following Structural Formula (3). The peropyrene compound is 1,3,8,10-tetrakis[N-phenyl-1-naphthylamino]peropyrene when $R^1$, $R^6$, $R^8$ and $R^{13}$ are each the group represented by following Structural Formula (4). The peropyrene compound is 1,3,8,10-tetrakis[4,4'-bis($\alpha,\alpha$-dimethylbenzyl)diphenylamino]peropyrene when $R^1$, $R^6$, $R^8$ and $R^{13}$ are each the group represented by following Structural Formula (5).

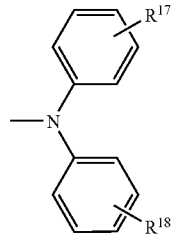

Structural Formula (3)

In Structural Formula (3), $R^{17}$ and $R^{18}$ may be the same as or different from each other and each represent one of hydrogen atom, an alkyl group and an aryl group. Examples of the alkyl group and the aryl group are as listed above.

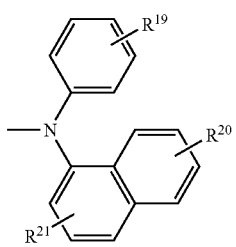

Structural Formula (4)

In Structural Formula (4), $R^{19}$, $R^{20}$ and $R^{21}$ may be the same as or different from one another and each represent one of hydrogen atom, an alkyl group and an aryl group. Examples of the alkyl group and the aryl group are as listed above.

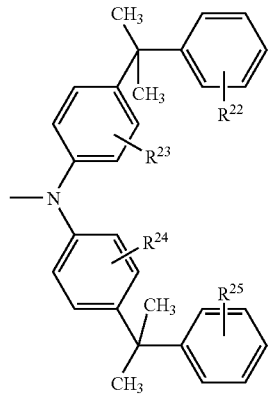

Structural Formula (5)

In Structural Formula (5), $R^{22}$, $R^{23}$, $R^{24}$ and $R^{25}$ may be the same as or different from one another and each represent one of hydrogen atom, an alkyl group and an aryl group. Examples of the alkyl group and the aryl group are as listed above.

The peropyrene compound of the present invention can be prepared by any suitable method appropriately selected from known preparation methods according to the purpose. The peropyrene compound is preferably prepared by a method described typically in Bericht vol. 76, page 458 (1943) and Journal of Chemical Society, page 2013 (1949). More specifically, a 1,3,8,10-tetrahalogenated peropyrene, for example, is initially synthetically prepared by adding perinaphthene and zinc powder to pyridine, stirring and refluxing the mixture, adding 50 ml of 80% acetic acid solution dropwise to the mixture under flow of nitrogen gas for five hours, filtrating the resulting precipitate, and dehydrating and sublimating the precipitate with the use of a vacuum sublimation apparatus to thereby yield unsubstituted peropyrene, and halogenating the peropyrene to yield the target compound.

The halogenation is preferably carried out by a method of adding 4 times by equivalent of a halogen to peropyrene dissolved in a solvent, as in the method described in Annalen der Chemie vol. 531, page 81. Preferred examples of the halogen are chlorine, bromine and iodine for advantageously carrying out the subsequent reaction, of which chlorine or bromine is preferred for easier halogenation. Next, the 1,3,8,10-tetrahalogenated peropyrene is allowed to react with, for example, a secondary amine corresponding to a target compound in the presence of a catalyst and a base with heating to thereby yield the target 1,3,8,10-tetra-substituted peropyrene compound.

Examples of the catalyst are copper or copper compounds such as copper powder, cuprous chloride and copper sulfate; and palladium compounds. Examples of the base are sodium carbonate, potassium carbonate, sodium hydroxide, and sodium alkoxides such as sodium t-butoxide.

To prepare 1,3,8,10-tetrakis(3-methyldiphenylamino) peropyrene according to the above-mentioned conventional procedure, peropyrene is initially allowed to react with bromine to yield 1,3,8,10-tetrabromoperopyrene. Next, 1,3,8,10-tetrabromoperopyrene is subjected to diarylamination by a method described in Tetrahedron Letters vol. 39, page 2367 (1998), namely a conventional method of preparing a triarylamine from a halogenated aryl. Specifically, to 1 equivalent of 1,3,8,10-tetrabromoperopyrene are added 4 times by equivalent of 3-methyldiphenylamine, 4 times by equivalent of sodium t-butoxide, 0.1 percent by equivalent of palladium acetate and 0.4 percent by equivalent of tri(t-butyl)phosphine, and the mixture is allowed to react in o-xylene as a solvent at 130° C. for three hours. After cooling, the reaction mixture is washed with water several times, o-xylene is distilled off, the residual oil is washed with methanol, and the reaction product is recrystallized from THF-methanol to yield a crude product. The crude product is purified by vacuum sublimation to thereby yield target 1,3,8,10-tetrakis(3-methyldiphenylamino)peropyrene.

The peropyrene compound of the present invention can be advantageously used in various regions, typically as a fluorescent material and more typically as a luminescent material in an organic electroluminescent element. The peropyrene compound of the present invention emits red light when used as a luminescent material in an organic electroluminescent element.

<Organic Electroluminescent Element>

The organic electroluminescent element of the present invention comprises a positive electrode, a negative electrode, and a thin organic layer arranged between the positive electrode and the negative electrode, in which the thin organic layer comprises the peropyrene compound of the present invention, namely the peropyrene compound represented by Structural Formula (1) as a luminescent material.

$R^1$, $R^6$, $R^8$ and $R^{13}$ (the groups represented by Structural Formula (2)) in Structural Formula (1) are preferably each the group represented by one of the Structural Formulae (3), (4) and (5), as described above.

The peropyrene compound contained as a luminescent material in the thin organic layer may be contained in a light-emitting layer or in another layer, such as a luminescent-electron-transporting layer which is a light-emitting layer also serve as the electron-transporting layer or a luminescent-hole-transporting layer which is a light-emitting layer also serve as the hole-transporting layer, of the thin organic layer. When the peropyrene compound is contained in the light-emitting layer, the light-emitting layer may comprise the peropyrene compound alone or may further comprise any other material in addition to the peropyrene compound.

It is preferred in the present invention that the light-emitting layer, luminescent-electron-transporting layer, luminescent-hole-transporting layer and other layers in the thin organic layer each comprise the peropyrene compound of the present invention as a guest material and further comprise, in addition to the guest material, a host material capable of emitting light with a wavelength near to the wavelength of optical absorption of the guest material. The host material is preferably contained in the light-emitting layer but may be contained in, for example, a hole-transporting layer and/or an electron-transporting layer.

When the guest material and the host material are used in combination for organic electroluminescence, the host material is initially excited. The excitation energy efficiently moves from the host material to the guest material, because the emission wavelength of the host material overlaps the absorption wavelength (330 to 600 nm) of the guest material (peropyrene compound). Thus, the host material returns to a ground state without light emission, and the guest material in an excited state alone emits the excitation energy as red light. This configuration is therefore excellent typically in emission efficiency, emission luminance and color purity of red light.

In general, when luminescent molecules are contained in a thin film alone or in a high concentration, the luminescent molecules are clouded and interact with each other to thereby induce decrease in emission efficiency, a phenomenon called as "concentration quenching". In the combination use of the guest material and the host material, however, the peropyrene compound serving as the guest compound is dispersed in the host compound in a relatively low concentration, and the "concentration quenching" is effectively prevented. Thus, the configuration advantageously achieves a high emission efficiency. The combination use of the guest material and the host material is typically advantageous in the light-emitting layer, since the host material generally has good film-forming property, and the light-emitting layer can be formed satisfactorily while maintaining the light emission properties.

The host material can be any material appropriately selected according to the purpose and is preferably one having an emission wavelength in the vicinity of the light absorption wavelength of the guest material. Preferred examples thereof are an aromatic amine derivative represented by following Structural Formula (6), a carbazole derivative represented by following Structural Formula (8), a hydroxyquinoline complex represented by following Structural Formula (10), a 1,3,6,8-tetraphenylpyrene compound represented by following Structural Formula (12), 4,4'-bis(2,2'-diphenylvinyl)-1,1'-biphenyl (DPVBi) represented by following Structural Formula (14) having principal emission wavelength of 470 nm, p-sesquiphenyl represented by following Structural Formula (15) having a principal emission wavelength of 400 nm and 9,9'-bianthryl represented by following Structural Formula (16) having a principal emission wavelength of 460 nm.

Structural Formula (6)

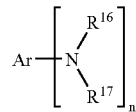

In Structural Formula (6), n is an integer of 2 to 4; Ar represents a divalent, trivalent or tetravalent aromatic or heteroaromatic group; and $R^{16}$ and $R^{17}$ may be the same as or different from each other and each represent a monovalent aromatic or heteroaromatic group. The monovalent aromatic or heteroaromatic group can be any suitable one selected according to the purpose.

Of the aromatic amine derivatives represented by Structural Formula (6), N,N'-dinaphthyl-N,N'-diphenyl-[1,1'-biphenyl]-4,4'-diamine (NPD) represented by following Structural Formula (7) having a principal emission wavelength of 430 nm and a derivative thereof are preferred.

Structural Formula (7)

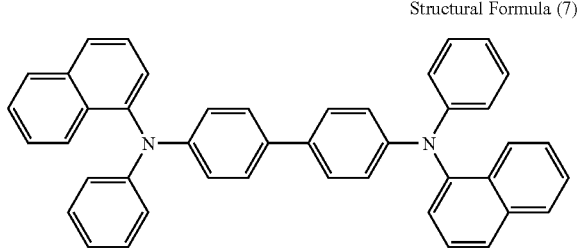

NPD

Structural Formula (8)

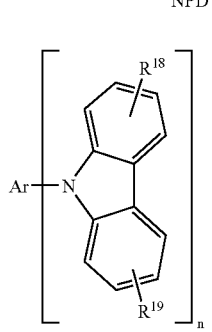

In Structural Formula (8), n is an integer of 2 to 4; and Ar represents the following divalent, trivalent or tetravalent group containing one or more aromatic rings or a divalent, trivalent or tetravalent group containing one or more heteroaromatic rings.

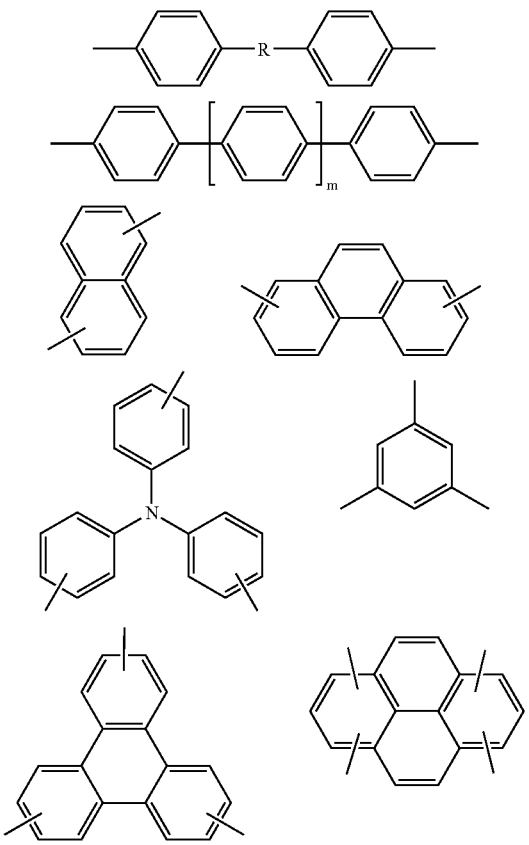

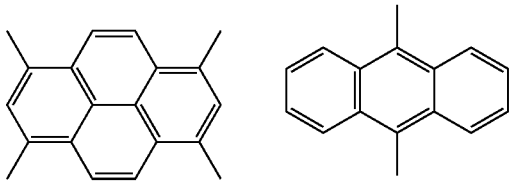

wherein m is 0 to 4

Each of these may be substituted with a disconjugate group; and R represents a linkage group, such as the following groups:

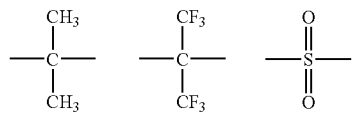

In Structural Formula (8), $R^{18}$ and $R^{19}$ are independently hydrogen atom, a halogen atom, an alkyl group, an aralkyl group, an alkenyl group, an aryl group, cyano group, amino group, an acyl group, an alkoxycarbonyl group, carboxyl group, an alkoxy group, an alkylsulfonyl group, hydroxy group, an amido group, an aryloxy group, an aromatic cyclic hydrocarbon group or an aromatic heterocyclic group, each of which may further be substituted with one or more substituents.

In Structural Formula (8), n represents an integer and is preferably an integer of 2 to 4.

Of the aromatic amine derivatives represented by Structural Formula (8), a compound wherein Ar is an aromatic group comprising two benzene rings bound to each other with the interposition of a single bond; $R^{18}$ and $R^{19}$ are hydrogen atoms; and n is 2, namely, 4,4'-bis(9-carbazolyl)-biphenyl (CBP) represented by following Structural Formula (9) having a principal emission wavelength of 380 nm, and a derivative thereof are preferred for satisfactory emission efficiency, emission luminance and color purity of red light.

Sturctural Formula (9)

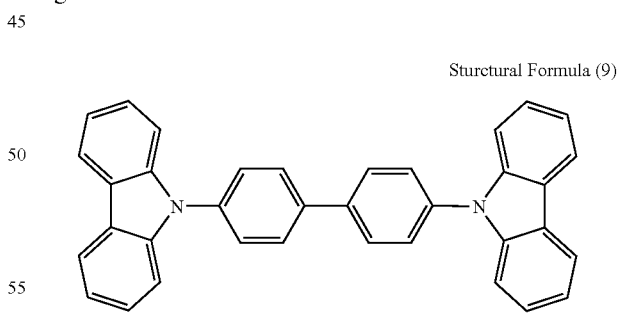

CBP

Structural Formula (10)

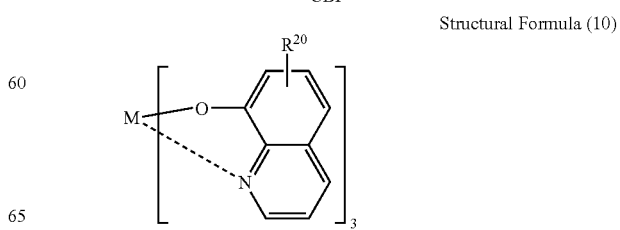

Of the hydroxyquinoline complexes represented by Structural Formula (10), aluminum hydroxyquinoline complex (Alq) represented by following Structural Formula (11) having a principal emission wavelength of 530 nm is preferred.

Structural Formula (11)

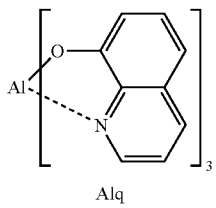

Alq

Structural Formula (12)

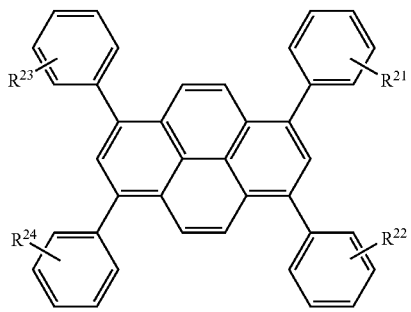

In Structural Formula (12), $R^{21}$ to $R^{24}$ may be the same as or different from each other and are each hydrogen atom or a substituent. Suitable examples of the substituent are an alkyl group, a cycloalkyl group and an aryl group, each of which may further be substituted with one or more substituents.

Of the 1,3,6,8-tetraphenylperopyrenes represented by Structural Formula (12), a compound wherein $R^{21}$ to $R^{24}$ are hydrogen atoms, namely, 1,3,6,8-tetraphenylperopyrene represented by following Structural Formula (13) having a principal emission wavelength of 440 nm is preferred for satisfactory emission efficiency, emission luminance and color purity of red light.

Structural Formula (13)

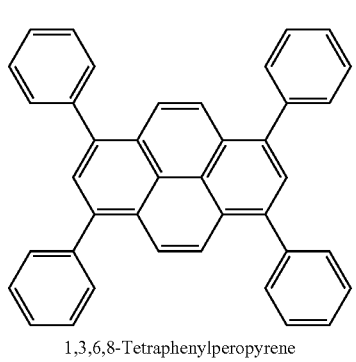

1,3,6,8-Tetraphenylperopyrene

-continued

Structural Formula (14)

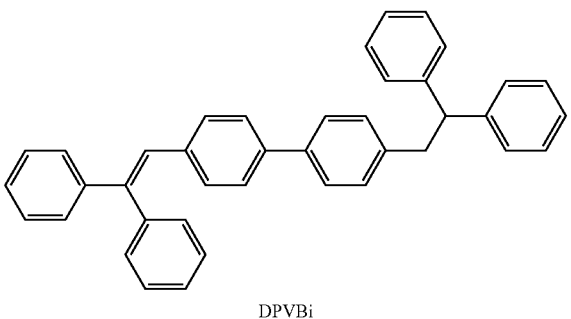

DPVBi

Structural Formula (15)

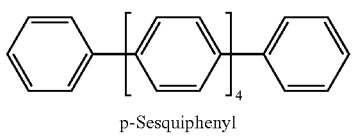

p-Sesquiphenyl

Structural Formula (16)

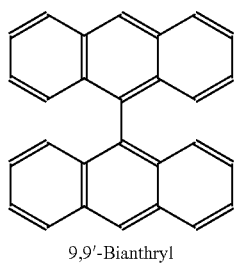

9,9'-Bianthryl

The content of the peropyrene compound represented by Structural Formula (1), if contained in a layer, is preferably 0.1 to 50 percent by weight and is more preferably 0.5 to 20 percent by weight.

If the content is less than 0.1 percent by weight, the emission efficiency, emission luminance, color purity and other properties may be insufficient. If it exceeds 50 percent by weight, the color purity may decrease. In contrast, the content within the above-specified preferred range is advantageous typically for excellent emission efficiency, emission luminance and color purity.

The light-emitting layer in the organic electroluminescent element of the present invention should serve, upon application of an electric field, to receive holes typically from the positive electrode, a hole-injecting layer or the hole-transporting layer, and electrons typically from the negative electrode, an electron-injecting layer or the electron-transporting layer, to provide a field of recombination between the holes and the electrons and to enable the peropyrene compound (luminescent material, luminescent molecules) to emit red light by the action of recombination energy generated upon the recombination. The light-emitting layer may further comprises any other luminescent material in addition to the peropyrene compound within ranges not deteriorating the emission of red light, as far as the layer exhibits the above functions.

The light-emitting layer can be prepared by any known method. Suitable examples of the method are vapor deposition, wet film formation, molecular beam epitaxy (MBE), ionized cluster beam technique, molecular stacking, Langmuir-Blodgett (LB) method, printing and transfer printing.

Among them, vapor deposition is preferred, because it can easily and efficiently produce the light-emitting layer at low cost without the use of an organic solvent and, in turn, without problems of waste treatment. The wet film formation, however, is also preferred when the light-emitting layer has a single-layer structure, such as a hole-transporting-luminescent-electron-transporting layer.

The vapor deposition can be any suitable vapor deposition technique selected according to the desired light-emitting layer and includes, for example, vacuum vapor deposition, resistance heating vapor deposition, chemical vapor deposition and physical vapor deposition. Examples of the chemical vapor deposition (CVD) are plasma CVD, laser CVD, thermal CVD and gas source CVD. The light-emitting layer can be formed according to the vapor deposition by, for example, subjecting the peropyrene compound to vacuum vapor deposition. When the light-emitting layer comprises the host material in addition to the peropyrene compound, the peropyrene compound and the host material are subjected simultaneous vacuum vapor deposition. The former technique achieves easy formation of the layer, since it does not require co-vapor deposition.

The wet film formation can be carried out by any suitable procedure selected according to the desired light-emitting layer. Examples of the procedure are an ink jet process, spin coating, kneader coating, bar coating, blade coating, casting, dipping and curtain coating.

According to the wet film formation, a solution comprising materials for the light-emitting layer with a resin component dissolved or dispersed in a solvent can be used (for example, be applied). Examples of the resin component are polyvinylcarbazoles, polycarbonates, poly(vinyl chloride)s, polystyrenes, poly(methyl methacrylate)s, polyesters, polysulfones, poly(phenylene oxide)s, polybutadienes, hydrocarbon resins, ketone resins, phenoxy resins, polyamides, ethyl cellulose, vinyl acetate, ABS resins, polyurethanes, melamine resins, unsaturated polyester resins, alkyd resins, epoxy resins and silicone resins.

The light-emitting layer can be suitably prepared according to the wet film formation, for example, by using a solution (coating composition) comprising the peropyrene compound and the resin material used according to necessity dissolved in a solvent, i.e., by applying and drying the coating composition. When the light-emitting layer comprises the host material in addition to the peropyrene compound, the light-emitting layer can be prepared by using a solution (coating composition) comprising the peropyrene compound, the host material and the resin material used according to necessity in a solvent, namely, by applying and drying the coating composition.

The thickness of the light-emitting layer is preferably 1 to 50 nm and more preferably 3 to 20 nm.

The thickness of the light-emitting layer within the above-specified preferred range provides sufficient emission efficiency, emission luminance and color purity of red light emitted by the organic electroluminescent element. These advantages are more significant when the thickness is within the above-specified more preferred range.

The organic electroluminescent element of the present invention comprises a positive electrode, a negative electrode and the thin organic layer containing the light-emitting layer and being arranged between the positive electrode and the negative electrode and may further comprise any other layers such as a protective layer.

The thin organic layer comprises at least the light-emitting layer and may further comprise any other layers such as a hole-injecting layer, a hole-transporting layer, a hole-blocking layer and/or an electron-transporting layer.

Positive Electrode

The positive electrode can be any suitable one selected according to the purpose and is preferably one capable of supplying holes (carrier) to the thin organic layer. More specifically, the positive electrode is preferably capable of supplying the carrier to the light-emitting layer when the thin organic layer comprises the light-emitting layer alone, to the hole-transporting layer when the thin organic layer further comprises the hole-transporting layer, and to the hole-injecting layer when the thin organic layer further comprises the hole-injecting layer.

The material for the positive electrode can be any suitable one selected according to the purpose and includes, for example, metals, alloys, metal oxides, electroconductive compounds, and mixtures of these materials. Among them, materials having a work function of 4 eV or more are preferred.

Specific examples of the material for the positive electrode are electroconductive metal oxides such as tin oxide, zinc oxide, indium oxide and indium tin oxide (ITO); metals such as gold, silver, chromium and nickel; mixtures or laminates of these metals and electroconductive metal oxides; inorganic electroconductive materials such as copper iodide and copper sulfide; organic electroconductive materials such as polyanilines, polythiophenes and polypyrroles; and laminates of these materials with ITO. Each of these can be used alone or in combination. Among them, electroconductive metal oxides are preferred, of which ITO is specifically preferred for its satisfactory productivity, high conductivity and transparency.

The thickness of the positive electrode can be suitably set typically according to the material and is preferably 1 to 5000 nm and more preferably 20 to 200 nm.

The positive electrode is generally arranged on a substrate made of, for example, glass such as soda lime glass or alkali-free glass, or a transparent resin.

The glass, if used as the substrate, is preferably the alkali-free glass, or the soda lime glass having a barrier coating such as silica coating for reducing ions dissolved from the glass.

The thickness of the substrate is not specifically limited, as long as the substrate can maintain certain mechanical strength. When the glass is used as the substrate, the thickness is generally 0.2 mm or more and preferably 0.7 mm or more.

The positive electrode can be formed, for example, by the above-mentioned method such as vapor deposition, wet film formation, electron beam technique, sputtering, reactive sputtering, molecular beam epitaxy (MBE), ionized cluster beam technique, ion plating, plasma polymerization (high-frequency excitation ion plating), molecular stacking, Langmuir-Blodgett (LB) method, printing, transfer printing and a method of applying a dispersion of ITO typically by a chemical reaction such as a sol-gel method.

The organic electroluminescent element can have a decreased drive voltage and/or an increased emission efficiency by subjecting the positive electrode to rinsing or another treatment. Suitable examples of the other treatment are UV-ozone treatment and plasma treatment when the positive electrode comprises ITO.

Negative Electrode

The negative electrode can be any suitable negative electrode selected according to the purpose and is preferably one capable of supplying electrons to the thin organic layer. More specifically, the negative electrode is preferably capable of supplying electrons to the light-emitting layer when the thin organic layer comprises the light-emitting layer alone, to the electron-transporting layer when the thin organic layer further comprises the electron-transporting layer, and to an electron-injecting layer when the thin organic layer comprises the electron-injecting layer between the thin organic layer and the negative electrode.

The material for the negative electrode is not specifically limited and can be appropriately selected typically according to adhesion with layers or molecules adjacent to the negative electrode, such as the electron-transporting layer and/or the light-emitting layer, ionization potential and stability. Examples of the material are metals, alloys, metal oxides, electroconductive compounds, and mixtures of these materials. Specific examples of the material for the negative electrode are alkali metals such as Li, Na, K and Cs, alkaline earth metals such as Mg and Ca, gold, silver, lead, aluminum, sodium-potassium alloys or mixed metals thereof, lithium-aluminum alloys or mixed metals thereof, magnesium-silver alloys or mixed metals thereof, rare earth metals such as indium and ytterbium, and alloys of these.

Each of these can be used alone or in combination. Among them, materials each having a work function of 4 eV or less are preferred, of which aluminum, lithium-aluminum alloy or mixed metals thereof, magnesium-silver alloy or mixed metals thereof are more preferred.

The thickness of the negative electrode can be freely set according typically to the material of the negative electrode and is preferably 1 to 10000 nm and more preferably 20 to 200 nm.

The negative electrode can be suitably prepared by any of the above-mentioned methods such as vapor deposition, wet film formation, electron beam technique, sputtering, reactive sputtering, molecular beam epitaxy (MBE), ionized cluster beam technique, ion plating, plasma polymerization (high-frequency excitation ion plating), molecular stacking, Langmuir-Blodgett (LB) method, printing or transfer printing.

When two or more different materials are used for the negative electrode, the two or more different materials may be subjected to vapor deposition simultaneously to form, for example, an alloy electrode, or an alloy previously prepared from the materials may be subjected to vapor deposition to form an alloy electrode.

The resistance of the positive electrode and the negative electrode is preferably as low as possible and is preferably several hundred ohms per square or less.

Hole-injecting Layer

The hole-injecting layer can be any suitable one selected according to the purpose and is preferably one capable of injecting holes from the positive electrode upon application of a voltage.

The material for the hole-injecting layer can be any suitable one selected according to the purpose, and suitable examples thereof are a starburst amine represented by the following formula (4,4',4''-tris[3-methylphenyl(phenyl) amino]triphenylamine: m-MTDATA), copper phthalocyanine and polyanilines.

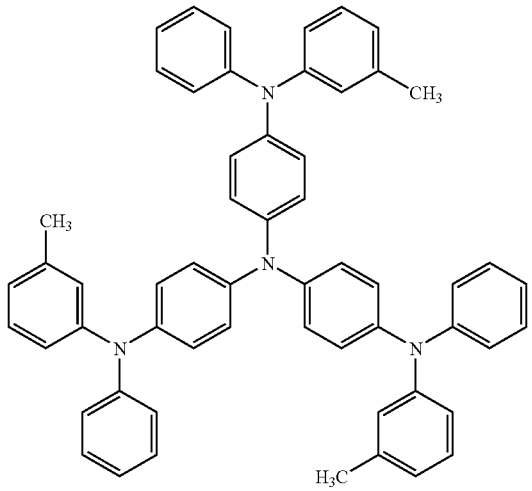

The thickness of the hole-injecting layer can be freely set according to the purpose and is preferably, for example, about 1 to about 100 nm and more preferably 5 to 50 nm.

The hole-injecting layer can be formed by any of the above-mentioned methods such as vapor deposition, wet film formation, electron beam technique, sputtering, reactive sputtering, molecular beam epitaxy (MBE), ionized cluster beam technique, ion plating, plasma polymerization (high-frequency excitation ion plating), molecular stacking, Langmuir-Blodgett (LB) method, printing or transfer printing.

Hole-transporting Layer

The hole-transporting layer can be any suitable one selected according to the purpose and is preferably one capable of transporting holes from the positive electrode upon application of a voltage.

The material for the hole-transporting layer can be any suitable one selected according to the purpose and includes, for example, aromatic amine compounds, carbazole, imidazole, triazole, oxazole, oxadiazole, polyarylalkanes, pyrazoline, pyrazolone, phenylenediamine, arylamines, amino-substituted chalcones, styrylanthracene, fluorenone, hydrazone, stilbene, silazane, styrylamine, aromatic dimethylidene compounds, porphyrin compounds, polysilane compounds, poly(N-vinylcarbazole)s, aniline copolymers, thiophene oligomers and polymers, polythiophenes and other electroconductive high-molecular oligomers and polymers and carbon films. A hole-transporting layer serving also as a light-emitting layer (i.e., hole-transporting-luminescent layer) can be prepared by mixing the material for the hole-transporting layer with a material for the light-emitting layer and forming a film of the mixture.

Each of these can be used alone or in combination. Among them, aromatic amine compounds are preferred, of which TPD (N,N'-diphenyl-N,N'-bis(3-methylphenyl)-[1,1'-biphenyl]-4,4'-diamine) represented by the following formula and NPD (N,N'-dinaphthyl-N,N'-diphenyl-[1,1'-biphenyl]-4,4'-diamine) represented by the following formula, for example, are more preferred.

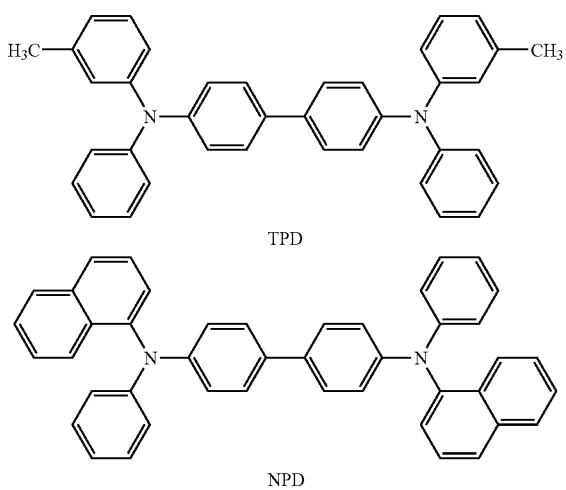

TPD

NPD

The thickness of the hole-transporting layer can be freely set according to the purpose and is generally 1 to 500 nm and preferably 10 to 100 nm.

The hole-transporting layer can be suitably prepared by any of the above-mentioned methods such as vapor deposition, wet film formation, electron beam technique, sputtering, reactive sputtering, molecular beam epitaxy (MBE), ionized cluster beam technique, ion plating, plasma polymerization (high-frequency excitation ion plating), molecular stacking, Langmuir-Blodgett (LB) method, printing or transfer printing.

Hole-Blocking Layer

The hole-blocking layer can be any suitable one selected according to the purpose and is preferably, for example, one capable of blocking holes injected from the positive electrode.

The material for the hole-blocking layer can be any suitable one selected according to the purpose.

When the organic electroluminescent element comprises the hole-blocking layer, holes transported from the positive electrode are blocked by the hole-blocking layer, and electrons transported from the negative electrode pass through the hole-blocking layer and reach the light-emitting layer. Thus, since the holes efficiently recombine with the electrons in the light-emitting layer, the recombination between the holes and the electrons in the other areas of the thin organic layer than the light-emitting layer is efficiently prevented, and the target peropyrene compound serving as a luminescent material efficiently emits light with good color purity. The hole-blocking layer is preferably arranged between the light-emitting layer and the electron-transporting layer.

The thickness of the hole-blocking layer can be freely set according to the purpose and is generally, for example, about 1 to about 500 nm and preferably 10 to 50 nm.

The hole-blocking layer may have a single-layer structure or a multilayered structure.

The hole-blocking layer can be prepared by any of the above-mentioned methods, such as vapor deposition, wet film formation, electron beam technique, sputtering, reactive sputtering, molecular beam epitaxy (MBE), ionized cluster beam technique, ion plating, plasma polymerization (high-frequency excitation ion plating), molecular stacking, Langmuir-Blodgett (LB) method, printing or transfer printing.

Electron-transporting Layer

The electron-transporting layer can be any suitable one selected according to the purpose and is preferably, for example, one having one of the functions of transporting electrons from the negative electrode and of blocking holes injected from the positive electrode.

The material for the electron-transporting layer can be any suitable one selected according to purpose and includes, for example, quinoline derivatives such as the aluminum hydroxyquinoline complex (Alq), oxadiazole derivatives, triazole derivatives, phenanthroline derivatives, perylene derivatives, pyridine derivatives, pyrimidine derivatives, quinoxaline derivatives, diphenylquinone derivatives and nitro-substituted fluorene derivatives. An electron-transporting layer serving also as a light-emitting layer (i.e., electron-transporting-luminescent layer) can be prepared by mixing the material for the electron-transporting layer with the material for the light-emitting layer and forming a film of the mixture. By further mixing a material for the hole-transporting layer and forming a film of the resulting mixture, an electron-transporting layer serving also as a hole-transporting layer and a light-emitting layer can be prepared. In this procedure, a polymer such as a polyvinylcarbazole or a polycarbonate can be used. The thickness of the electron-transporting layer can be freely set according to the purpose and is generally, for example, about 1 to about 500 nm and preferably 10 to 50 nm.

The electron-transporting layer may have a single-layer structure or a multilayered structure.

An electron transporting material for the electron-transporting layer arranged adjacent to the light-emitting layer is preferably one having a wavelength of optical absorption edge shorter than that of the peropyrene compound. This limits a light emission area in the organic electroluminescent element to the light-emitting layer and prevents extra light emission from the electron-transporting layer. Examples of the electron transporting material having the wavelength of optical absorption edge shorter than that of the peropyrene compound are phenanthroline derivatives, oxadiazole derivatives and triazole derivatives, of which the following compounds are preferred.

Structural Formula (17)

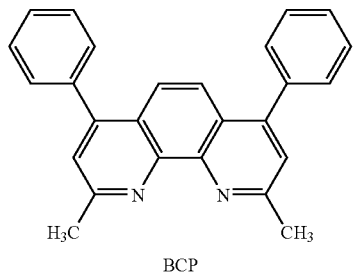

BCP

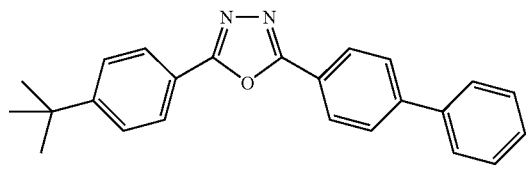

2-(4-tert-Butylphenyl)-5-(4-biphenylyl)-1,3,4-oxadiazole

-continued

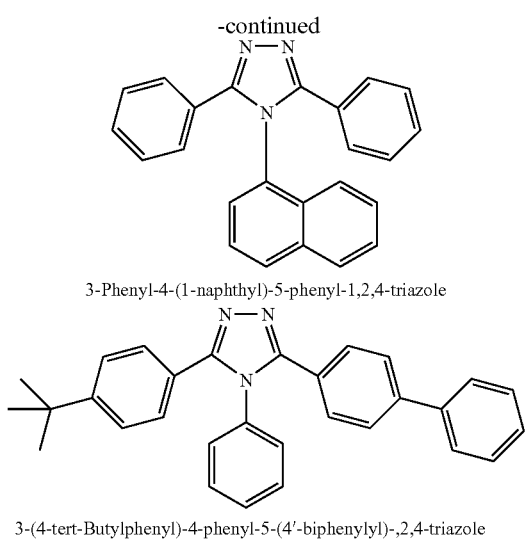

3-Phenyl-4-(1-naphthyl)-5-phenyl-1,2,4-triazole 3-(4-tert-Butylphenyl)-4-phenyl-5-(4'-biphenylyl)-,2,4-triazole The electron-transporting layer can be suitably prepared by any of the above-mentioned methods, such as vapor deposition, wet film formation, electron beam technique, sputtering, reactive sputtering, molecular beam epitaxy (MBE), ionized cluster beam technique, ion plating, plasma polymerization (high-frequency excitation ion plating), molecular stacking, Langmuir-Blodgett (LB) method, printing or transfer printing.

Other Layers

The organic electroluminescent element of the present invention may further comprise any other layers selected according to the purpose. An suitable example of the other layers is a protective layer.

The protective layer can be any suitable one selected according to the purpose and is preferably, for example, one capable of preventing a molecule or substance which deteriorates the organic electroluminescent element, such as moisture or oxygen, from coming into the organic electroluminescent element.

Examples of the material for the protective layer are metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; nitrides such as SiN and $SiN_xO_y$; metal fluorides such as $MgF_2$, LiF, $AlF_3$ and $CaF_2$; polyethylenes, polypropylenes, poly(methyl methacrylate)s, polyimides, polyureas, polytetrafluoroethylenes, polychlorotrifluoroethylenes, polydichlorodifluoroethylenes, copolymers of chlorotrifluoroethylene with dichlorodifluoroethylene, copolymers prepared by copolymerizing a monomer mixture comprising tetrafluoroethylene and at least one comonomer, fluorine-containing copolymers each having a cyclic structure in a principal chain thereof, water-absorptive substances having a percentage of water absorption of 1% or more, and moisture-proof substances having a percentage of water absorption of 0.1% or less.

The protective layer can be prepared by any of the above-mentioned methods such as vapor deposition, wet film formation, sputtering, reactive sputtering, molecular beam epitaxy (MBE), ionized cluster beam technique, ion plating, plasma polymerization (high-frequency excitation ion plating), printing or transfer printing.

The structure of the organic electroluminescent element of the present invention can be any suitable one selected according to the purpose. Suitable examples of the layer configuration thereof are the following layer configurations (1) to (13): (1) positive electrode/hole-injecting layer/hole-transporting layer/light-emitting layer/electron-transporting layer/electron-injecting layer/negative electrode, (2) positive electrode/hole-injecting layer/hole-transporting layer/light-emitting layer/electron-transporting layer/negative electrode, (3) positive electrode/hole-transporting layer/light-emitting layer/electron-transporting layer/electron-injecting layer/negative electrode, (4) positive electrode/hole-transporting layer/light-emitting layer/electron-transporting layer/negative electrode, (5) positive electrode/hole-injecting layer/hole-transporting layer/luminescent-electron-transporting layer/electron-injecting layer/negative electrode, (6) positive electrode/hole-injecting layer/hole-transporting layer/luminescent-electron-transporting layer/negative electrode, (7) positive electrode/hole-transporting layer/luminescent-electron-transporting layer/electron-injecting layer/negative electrode, (8) positive electrode/hole-transporting layer/luminescent-electron-transporting layer/negative electrode, (9) positive electrode/hole-injecting layer/hole-transporting-light-emitting layer/electron-transporting layer/electron-injecting layer/negative electrode, (10) positive electrode/hole-injecting layer/hole-transporting-light-emitting layer/electron-transporting layer/negative electrode, (11) positive electrode/hole-transporting-light-emitting layer/electron-transporting layer/electron-injecting layer/negative electrode, (12) positive electrode/hole-transporting-light-emitting layer/electron-transporting layer/negative electrode, and (13) positive electrode/hole-transporting-luminescent-electron-transporting layer/negative electrode.

When the organic electroluminescent element further comprises the hole-blocking layer, the hole-blocking layer is preferably arranged between the light-emitting layer and the electron-transporting layer in any of the layer configurations (1) to (13).

Among these layer configurations, an aspect of the layer configuration (4) positive electrode/hole-transporting layer/light-emitting layer/electron-transporting layer/negative electrode is illustrated in FIG. 1. An organic electroluminescent element 10 has a layer configuration comprising a glass substrate 12, a positive electrode 14 (for example, an indium tin oxide electrode), a hole-transporting layer 16, a light-emitting layer 18, an electron-transporting layer 20 and a negative electrode 22 (for example, an Al—Li electrode) arranged in this order. The positive electrode 14, such as an indium tin oxide electrode, and the negative electrode 22, such as an Al—Li electrode, are connected to each other via a power source. The hole-transporting layer 16, the light-emitting layer 18 and the electron-transporting layer 20 constitute a thin organic layer 24 for emitting red light.

The emission peak wavelength of the organic electroluminescent element of the present invention is preferably 580 to 700 nm.

Regarding emission efficiency, the organic electroluminescent element of the present invention is preferably capable of emitting red light at voltages of 10 V or less, more preferably at voltages of 7 V or less, and specifically preferably at voltages of 5 V or less.

The emission luminance of the organic electroluminescent element of the present invention is preferably 100 $cd/m^2$ or more, more preferably 500 $cd/m^2$ or more and specifically preferably 1000 $cd/m^2$ or more at an applied voltage of 10 V. The organic electroluminescent element of the present invention can be suitable used in a variety of regions such as computers, on-vehicle displays, field displays, household appliances, commercial equipment, household electric equipment, displays for transit, clock displays, calendar displays, luminescent screens and audio equipment. It can be specifically preferably used for the organic electroluminescent display of the present invention.

<Organic Electroluminescent Display>

The organic electroluminescent display of the present invention is not specifically limited and can have any suitable known configuration, as long as it comprises the organic electroluminescent element of the present invention.

The organic electroluminescent display may be configured so as to emit red light alone, to emit light of a plurality of colors or to emit full-color light.

Examples of a method for providing a full-color organic electroluminescent display include a three-color light emitting method of disposing organic electroluminescent elements each emitting light corresponding to the three primary colors, red (R), green (G) or blue (B) light, on a substrate, a white color method of separating white light from a white light emitting organic electroluminescent element into three primary colors through a color filter, and a color conversion method of converting blue light from a blue light emitting organic electroluminescent element into red (R) and green (G) colors through a fluorescent dye layer, as described typically in "Monthly Display", the September 2000 issue, pages 33–37. In the present invention using the organic electroluminescent element of the present invention for emitting red light, the three-color light emitting method or the color conversion method is preferably employed, of which the three-color light emitting method is specifically preferably employed.

Providing a full-color organic electroluminescent display by the three-color light emitting method requires an organic electroluminescent element for emitting green light and an organic electroluminescent element for emitting blue light, in addition to the organic electroluminescent element of the present invention for emitting red light.

The organic electroluminescent element for emitting green light can be any suitable one selected from known elements according to the purpose and is preferably one having a layer configuration of ITO (positive electrode)/NPD/Alq/Al—Li (negative electrode).

The organic electroluminescent element for emitting blue light can be any suitable one selected from known elements according to the purpose and is preferably, for example, one having a layer configuration of ITO (positive electrode)/NPD/DPVBi/Alq/Al—Li (negative electrode).

The configuration of the organic electroluminescent display can be any suitable one selected according to the purpose and may be, for example, a passive-matrix panel or an active-matrix panel as described in "Nikkei Electronics", No. 765, the Mar. 13, 2000 issue, pages 55 to 62.

Figure 2:
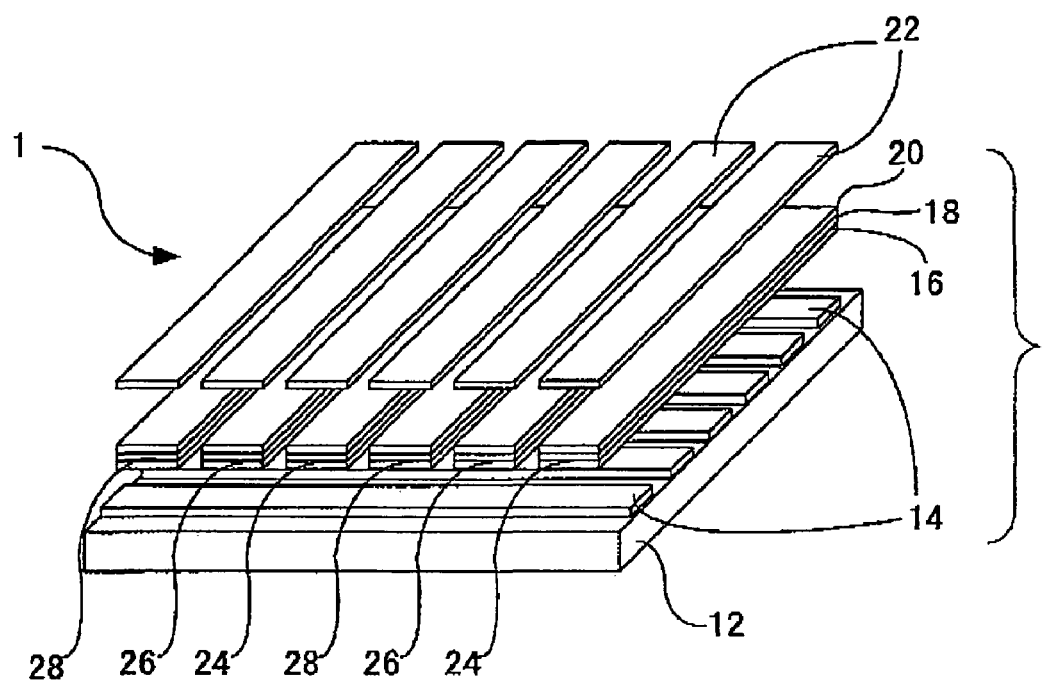
FIG. 2 is a schematic diagram illustrating an example of the structure of a passive-matrix organic electroluminescent display (passive-matrix panel).
Figure 3:
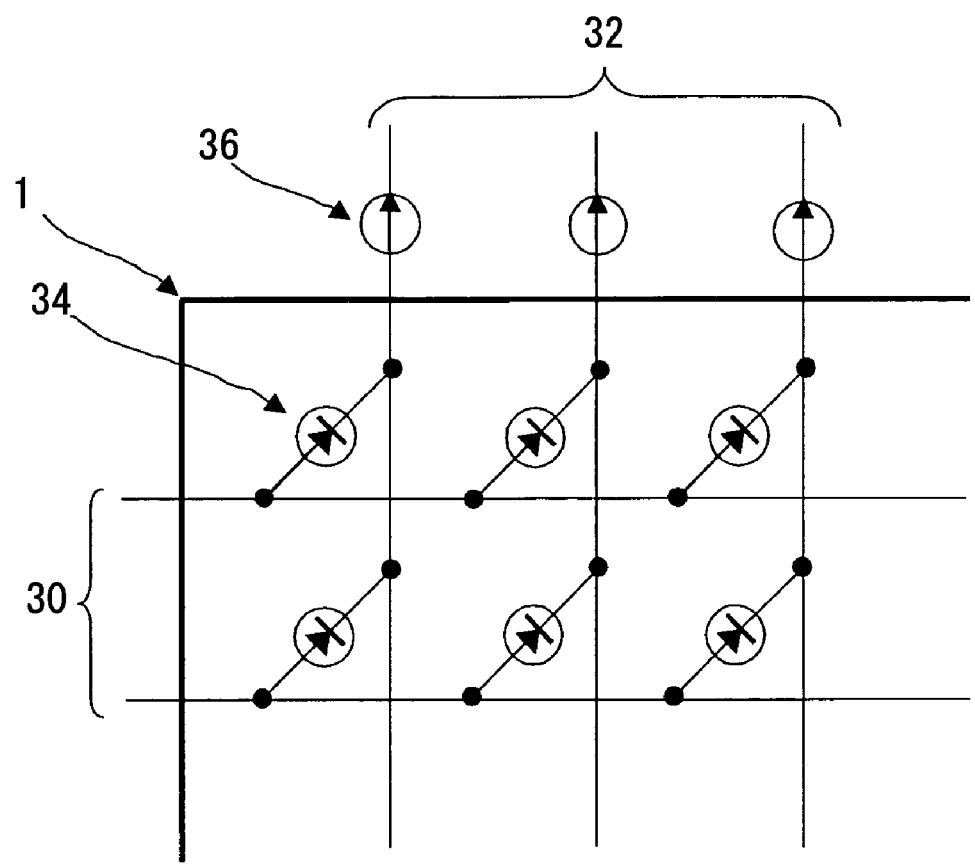
FIG. 3 is a schematic diagram illustrating an example of circuitry of the passive-matrix organic electroluminescent display (passive-matrix panel) shown in FIG. 2.

The passive-matrix panel comprises, for example, a glass substrate 12, positive electrodes 14 (for example, indium tin oxide electrodes), a thin organic layer 24 for emitting red light, a thin organic layer 26 for emitting blue light, a thin organic layer 28 for emitting green light, and negative electrodes 22 (FIG. 2). The positive electrodes 14 each have a narrow shape, are arranged in parallel with each other on the glass substrate 12. The thin organic layer 24 for emitting red light, the thin organic layer 26 for emitting blue light and the thin organic layer 28 for emitting green light are arranged in parallel with one another in turn on the positive electrodes 14 in a direction substantially perpendicular to the positive electrodes 14. The negative electrodes 22 are arranged on the thin organic layer 24 for emitting red light, the thin organic layer 26 for emitting blue light and the thin organic layer 28 for emitting green light and have the same shape with these thin layers.

In the passive-matrix panel, positive electrode lines 30 each having plural positive electrodes 14 intersect negative electrode lines 32 each having plural negative electrodes 22 in a substantially perpendicular direction to form a circuit. The thin organic layers 24, 26 and 28 for emitting red, blue and green light, respectively, are arranged at intersections and serve as pixels. Plural organic electroluminescent elements 34 are arranged corresponding to the respective pixels. Upon application of a current by a constant-current power supply 36 on one of the positive electrodes 14 in the positive electrode lines 30 and one of the negative electrodes 22 in the negative electrode lines 32 in the passive-matrix panel, the current is applied on an organic electroluminescent thin layer at the intersection between the lines to allow the organic electroluminescent thin layer at the position to emit light. By controlling light emission of each pixel independently, a full-color image can be easily produced.

Figure 4:
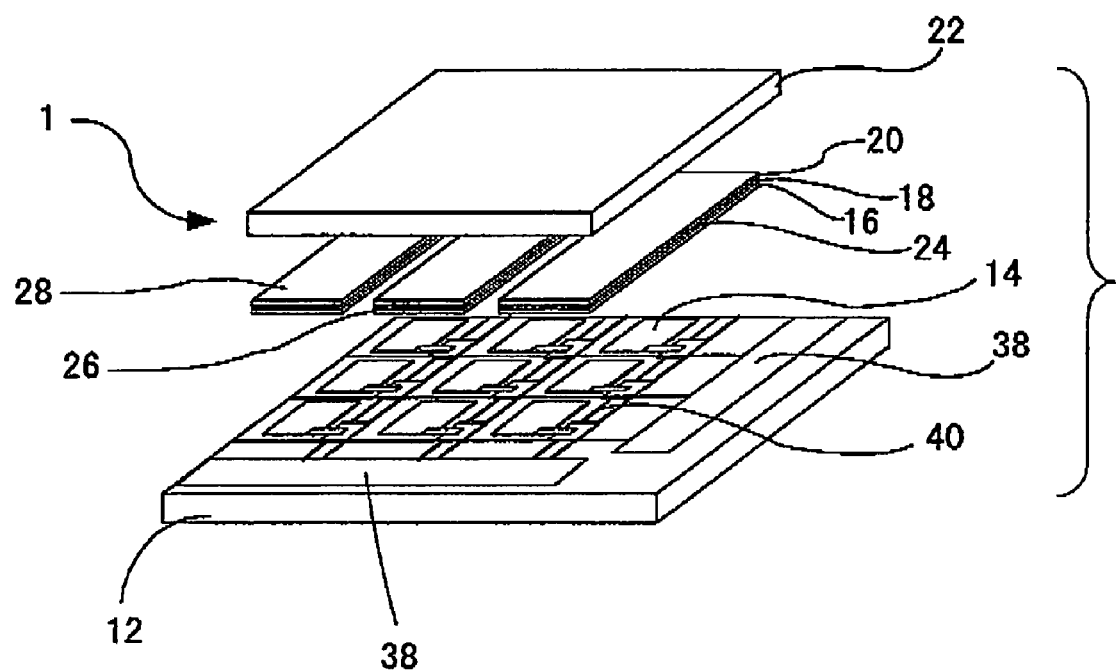
FIG. 4 is a schematic diagram illustrating an example of the structure of an active-matrix organic electroluminescent display (active-matrix panel).

With reference to FIG. 4, the active-matrix panel comprises, for example, a glass substrate 12, scanning lines, data lines and current supply lines, TFT circuits 40, and positive electrodes 14. The scanning lines, data lines and current supply lines are arranged on the glass substrate 12 as grids in a rectangular arrangement. The TFT circuits 40 are connected typically to the scanning lines constituting the grids and are arranged in each grid. The positive electrodes 14 may be, for example, indium tin oxide electrodes, are capable of being driven by the TFT circuits 40 and are arranged in each grid. An thin organic layer 24 for emitting red light, a thin organic layer 26 for emitting blue light and a thin organic layer 28 for emitting green light each have a narrow shape and are arranged in parallel with each other in turn on the positive electrodes 14. A negative electrode 22 is arranged so as to cover the thin organic layer 24 for emitting red light, the thin organic layer 26 for emitting blue light and the thin organic layer 28 for emitting green light. The thin organic layer 24 for emitting red light, the thin organic layer 26 for emitting blue light and the thin organic layer 28 for emitting green light each comprise a hole-transporting layer 16, a light-emitting layer 18 and an electron-transporting layer 20.

Figure 5:
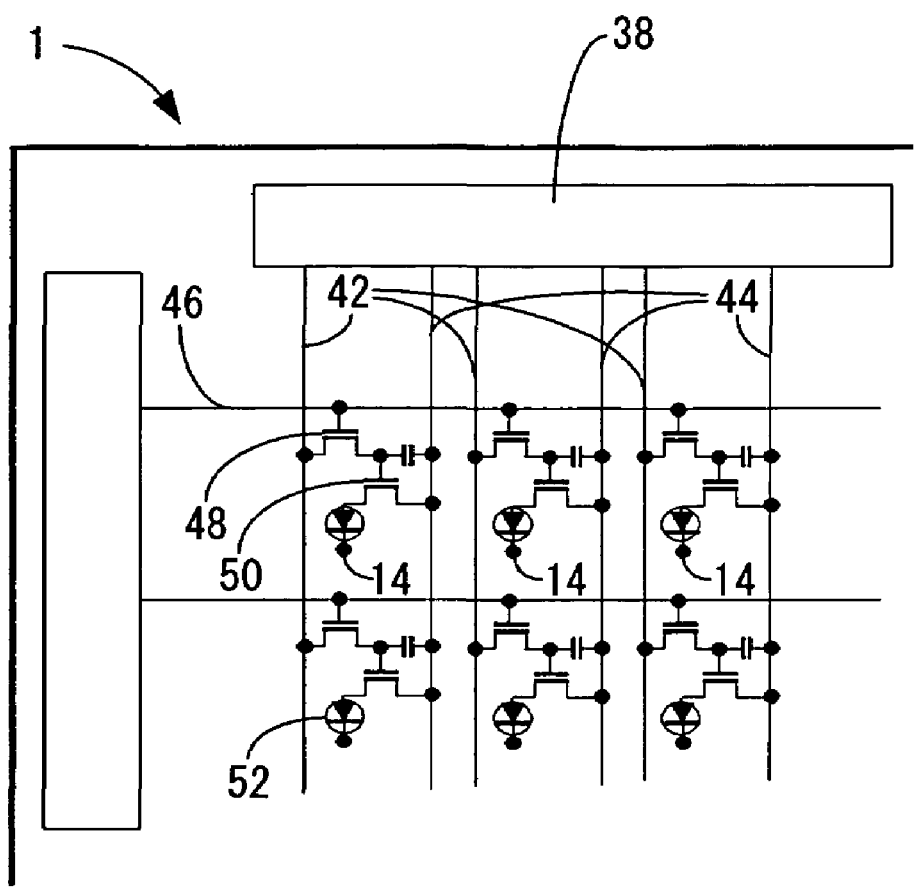
FIG. 5 is a schematic diagram illustrating an example of the circuitry of the active-matrix organic electroluminescent display (active-matrix panel) shown in FIG. 4.

In the active-matrix panel, for example as shown in FIG. 5, scanning lines 46 intersect with data lines 42 and current-supply lines 44 in a perpendicular direction to form grids in a rectangular arrangement. The scanning lines 46 are arranged in parallel with one another. The data lines 42 and current-supply lines 44 are arranged in parallel with one another. A switching TFT 48 and a drive TFT 50 are arranged in each grid to form a circuit. The switching TFT 48 and the drive TFT 50 in each grid can be independently derived by the application of a current by a drive circuit 38. In each grid, the organic thin film elements 24, 26 and 28 for emitting red, blue and green light, respectively serve as pixels. Upon application of a current from the drive circuit 38 to one of the scanning lines 46 arranged in a lateral direction and to the current-supply lines 44 arranged in a vertical direction, a switching TFT positioned at the intersection operates to drive the drive TFT 50 to allow an organic electroluminescent element 52 at the position to emit light. By controlling light emission of each pixel independently, a full-color image can be easily produced.

The organic electroluminescent display of the present invention can be suitable used in a variety of regions such as computers, on-vehicle displays, field displays, household appliances, commercial equipment, household electric equipment, displays for transit, clock displays, calendar displays, luminescent screens and audio equipment.

The present invention will be illustrated in further detail with reference to several examples below, which are not intended to limit the scope of the present invention.

EXAMPLE 1

Synthesis of 1,3,8,10-tetrakis(3-methyldiphenylamino)peropyrene

With reference to the following scheme, perinaphthene and zinc powder were added to pyridine (I in the following synthesis scheme), 50 ml of 80% acetic acid was added dropwise thereto with stirring under reflux in nitrogen flow over five hours, the resulting precipitate (II in the following synthesis scheme I) was filtrated, was dehydrated and sublimated using a vacuum sublimation apparatus and thereby yielded unsubstituted peropyrene (III in the following synthesis scheme).

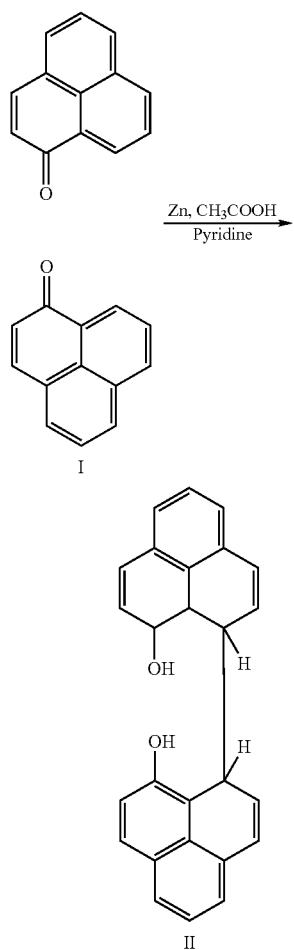

Next, 1,3,8,10-tetrabromoperopyrene (IV in the following scheme) was synthetically prepared by bromination of the unsubstituted peropyrene (refer to the following scheme). The bromination was carried out by adding 4 times by equivalent of elementary bromine to a solution of 1 equivalent of peropyrene in a solvent, as described in Annalen der Chemie, vol. 531, page 81.

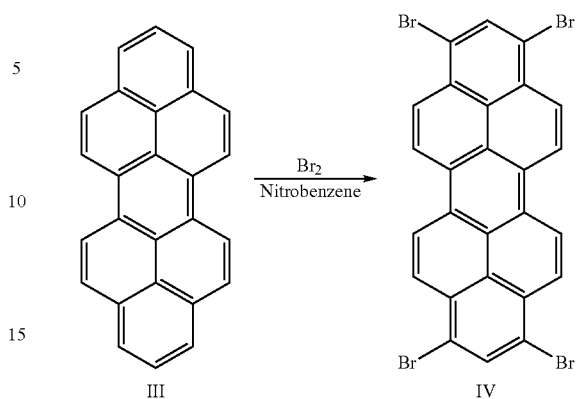

Next, to the above-prepared 1,3,8,10-tetrabromoperopyrene were added 4 times by equivalent of 3-methyldiphenylamine, 4 times by equivalent of sodium t-butoxide, 0.1 percent by equivalent of palladium acetate, 0.4 percent by equivalent of tri(t-butyl)phosphine and o-xylene as a solvent, and the mixture was reacted at 130° C. for three hours, according to the following scheme. After cooling, the reaction mixture was washed with water several times, and o-xylene was distilled off. The residual oil was washed with methanol, and the reaction product was recrystallized from THF-methanol to thereby yield a crude product. The crude product was purified by vacuum sublimation and thereby yielded target 1,3,8,10-tetrakis(3-methyldiphenylamino) peropyrene.

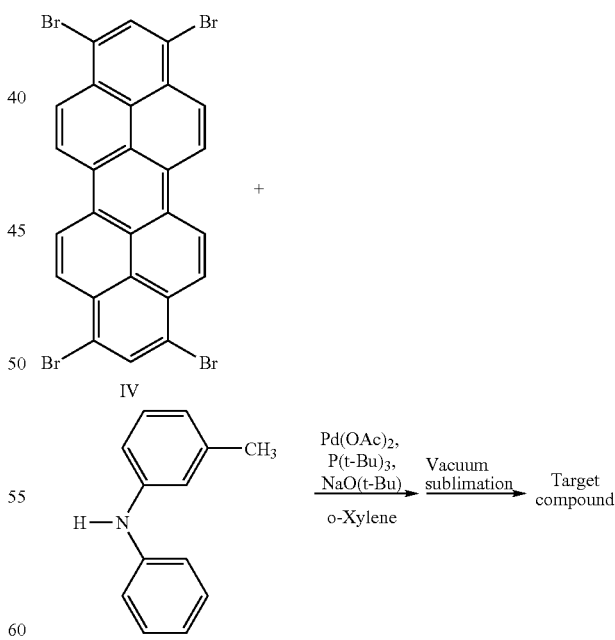

1,3,8,10-tetrakis(3-methyldiphenylamino)peropyrene is a compound of Structural Formula (1) wherein $R^1$, $R^6$, $R^8$ and $R^{13}$ are the same as one another and are each a group represented by the following structural formula; and $R^2$ to $R^5$, $R^7$, $R^9$ to $R^{12}$ and $R^{14}$ are hydrogen atoms.

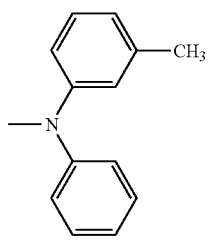

EXAMPLE 2

Synthesis of 1,3,8,10-tetrakis[N-phenyl-1-naphthylamino]peropyrene

By the procedure of Example 1 was prepared 1,3,8,10-tetrakis[N-phenyl-1-naphthylamino]peropyrene, except for using N-phenyl-1-naphthylamine instead of 3-methyldiphenylamine. The 1,3,8,10-tetrakis[N-phenyl-1-naphthylamino]peropyrene is a compound of Structural Formula (1) wherein $R^1$ to $R^4$ are each a group represented by the following structural formula:

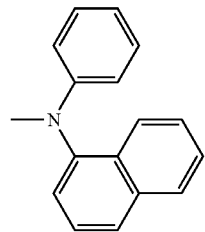

The results in mass spectrometry, elementary analysis and IR analysis of the above-prepared 1,3,8,10-tetrakis[N-phenyl-1-naphthylamino]peropyrene are as follows.

<Result in Mass Spectrometry>
Calculated molecular weight as $C_{90}H_{58}N_4$ (assuming that C12, H:1 and N:14): 1194
Peak in molecular weight in mass spectrometry: 1194, 1195

<Result in Elementary Analysis>
As $C_{90}H_{58}N_4$,
Calculated value C:90.42%; H:4.89%; N:4.69%
Experimental value C:90.18%; H:5.43%; N:4.38%

Figure 6:
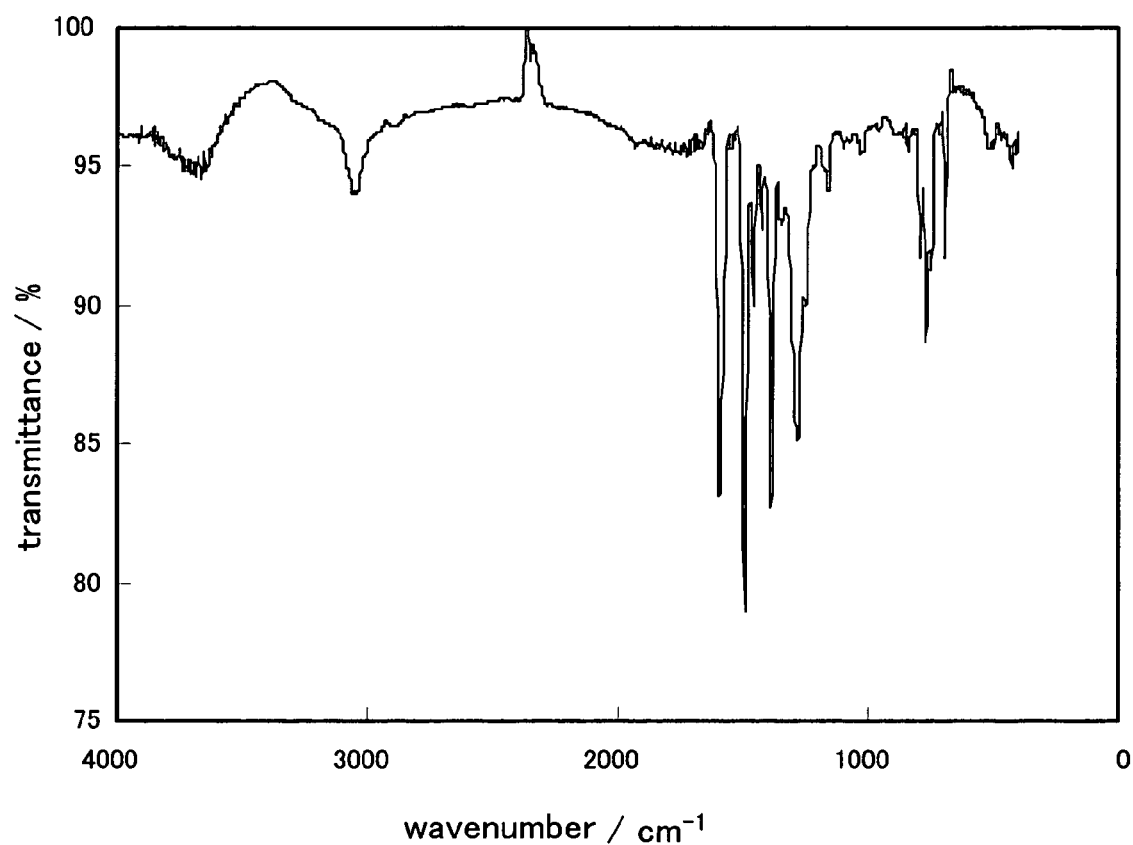
FIG. 6 is a chart of the infrared spectrum of synthesized 1,3,8,10-tetrakis[N-phenyl-1-naphthylamino]peropyrene.

<Result in IR Analysis>
The IR spectrum of the above-prepared 1,3,8,10-tetrakis[N-phenyl-1-naphthylamino]peropyrene according to a potassium bromide tablet method is shown in FIG. 6.

EXAMPLE 3

Synthesis of 1,3,8,10-tetrakis[4,4'-bis(α,α-dimethylbenzyl)diphenylamino]peropyrene By the procedure of Example 1 was synthetically prepared 1,3,8,10-tetrakis[4,4'-bis(α,α-dimethylbenzyl)diphenylamino]peropyrene, except for using 4,4'-bis(α,α-dimethylbenzyl)diphenylamine instead of 3-methyldiphenylamine. The prepared 1,3,8,10-tetrakis[4,4'-bis(α,α-dimethylbenzyl) diphenylamino]peropyrene is a compound of Structural Formula (1) wherein $R^1$ to $R^4$ are each a group represented by the following structural formula:

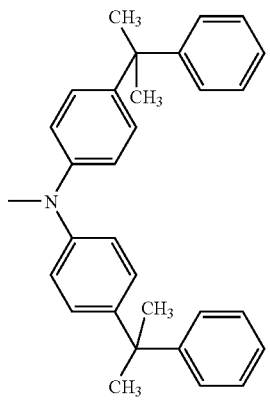

EXAMPLE 4

Preparation of Organic Electroluminescent Element

A multilayered organic electroluminescent element using 1,3,8,10-tetrakis(3-methyldiphenylamino)peropyrene prepared according to Example 1 as a luminescent material in a light-emitting layer was prepared in the following manner. Initially, a glass substrate having an indium tin oxide electrode as a positive electrode was subjected to ultrasonic cleaning with water, acetone and isopropyl alcohol and to UV ozone treatment. A layer of N,N'-dinaphthyl-N,N'-diphenyl-[1,1'-biphenyl]-4,4'-diamine (NPD) serving as a hole-transporting layer 50 nm thick was formed on the indium tin oxide electrode using a vacuum vapor deposition apparatus at a degree of vacuum of $1\times10^{-6}$ Torr ($1.3\times10^{-4}$ Pa) and a temperature of the substrate of room temperature. A layer of 1,3,8,10-tetrakis(3-methyldiphenylamino)peropyrene serving as a light-emitting layer 30 nm thick was formed by vapor deposition on the hole-transporting layer comprising N,N'-dinaphthyl-N,N'-diphenyl-[1,1'-biphenyl]-4,4'-diamine (NPD). Then a layer of aluminum hydroxyquinoline complex (Alq) serving as an electron-transporting layer 20 nm thick was formed on the light-emitting layer by vapor deposition, and a layer of an Al—Li alloy having a Li content of 0.5 percent by weight serving as a negative electrode was formed to a thickness of 50 nm by vapor deposition on the electron-transporting layer comprising the aluminum hydroxyquinoline complex (Alq). Thus, the organic electroluminescent element was prepared.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light having an emission luminance of 1350 cd/m² was observed at an applied voltage of 10 V.

EXAMPLE 5

Preparation of Organic Electroluminescent Element

An organic electroluminescent element was prepared by the procedure of Example 4, except for forming the light-emitting layer by simultaneous vapor deposition of 1,3,8, 10-tetrakis(3-methyldiphenylamino)peropyrene and N,N'- dinaphthyl-N,N'-diphenyl-[1,1'-biphenyl]-4,4'-diamine (NPD) at a ratio of the vapor deposition rate of the former to that of the latter of 1:99.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 1820 cd/m$^2$ was observed at an applied voltage of 10 V.

EXAMPLE 6

Preparation of Organic Electroluminescent Element

An organic electroluminescent element was prepared by the procedure of Example 4, except for forming the light-emitting layer by simultaneous vapor deposition of 1,3,8,10-tetrakis(3-methyldiphenylamino)peropyrene and 4,4'-bis(9-carbazolyl)-biphenyl (CBP) at a ratio of the vapor deposition rate of 1,3,8,10-tetrakis(3-methyldiphenylamino)peropyrene to that of CBP of 1:99.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 1890 cd/m$^2$ was observed at an applied voltage of 10 V.

EXAMPLE 7

Preparation of Organic Electroluminescent Element

An organic electroluminescent element was prepared by the procedure of Example 4, except for forming the light-emitting layer by simultaneous vapor deposition of 1,3,8,10-tetrakis(3-methyldiphenylamino)peropyrene and aluminum hydroxyquinoline complex (Alq) at a ratio of the vapor deposition rate of 1,3,8,10-tetrakis(3-methyldiphenylamino)peropyrene to that of Alq of 1:99.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 2040 cd/m$^2$ was observed at an applied voltage of 10 V.

EXAMPLE 8

Preparation of Organic Electroluminescent Element

An organic electroluminescent element was prepared by the procedure of Example 4, except for using 1,3,8,10-tetrakis[N-phenyl-1-naphthylamino]peropyrene prepared according to Example 2 instead of 1,3,8,10-tetrakis(3-methyldiphenylamino)peropyrene prepared according to Example 1.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 1480 cd/m$^2$ was observed at an applied voltage of 10 V.

EXAMPLE 9

Preparation of Organic Electroluminescent Element

An organic electroluminescent element was prepared by the procedure of Example 8, except for forming the light-emitting layer by simultaneous vapor deposition of 1,3,8,10-tetrakis[N-phenyl-1-naphthylamino]peropyrene and aluminum hydroxyquinoline complex (Alq) at a ratio of the vapor deposition rate of the 1,3,8,10-tetrakis[N-phenyl-1-naphthylamino]peropyrene to that of Alq of 1:99.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 2030 cd/m$^2$ was observed at an applied voltage of 10 V.

EXAMPLE 10

Preparation of Organic Electroluminescent Element

An organic electroluminescent element was prepared by the procedure of Example 8, except forming a hole-transporting-light-emitting layer having a thickness of 50 nm with the use of 1,3,8,10-tetrakis[N-phenyl-1-naphthylamino]peropyrene, instead of forming the hole-transporting layer.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 1440 cd/m$^2$ was observed at an applied voltage of 10 V.

EXAMPLE 11

Preparation of Organic Electroluminescent Element

An organic electroluminescent element was prepared by the procedure of Example 9, except for using 1,3,8,10-tetrakis[4,4'-bis(α,α-dimethylbenzyl)diphenylamino]peropyrene prepared according to Example 3 instead of 1,3,8,10-tetrakis[N-phenyl-1-naphthylamino]peropyrene.

Upon application of a voltage to the indium tin oxide electrode (positive electrode) and the Al—Li alloy (negative electrode) in the above-prepared organic electroluminescent element, emission of red light was observed at voltages of 5 V or more, and emission of high-purity red light at an emission luminance of 2100 cd/m$^2$ was observed at an applied voltage of 10 V.

The present invention can solve problems in conventional technologies and provide a peropyrene compound which is suitable as a red-light emitting material in an organic electroluminescent element, an organic electroluminescent element excellent typically in emission efficiency, emission luminance and color purity of red light, and a high-performance organic electroluminescent display using the organic electroluminescent element.

What is claimed is:
1. An organic electroluminescent element comprising:
a positive electrode,
a negative electrode, and
a thin organic layer arranged between the positive electrode and the negative electrode, wherein the thin organic layer comprises, as a luminescent material, a peropyrene compound represented by following Structural Formula (1):

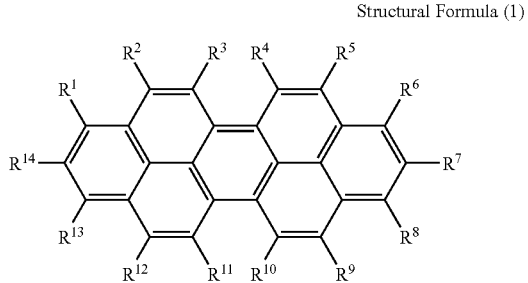

Structural Formula (1)

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent hydrogen atom or a substituent:

Structural Formula (2)

wherein $R^{15}$ and $R^{16}$ may be the same as or different from each other and each represent one of hydrogen atom, an alkyl group and an aryl group, where $R^{15}$ and $R^{16}$ may be bound to each other directly or indirectly.

2. An organic electroluminescent element according to claim 1, wherein the peropyrene compound is a substituted or unsubstituted 1,3,8,10-tetrakis(N,N-diphenylamino)peropyrene, wherein $R^1$, $R^6$, $R^8$ and $R^{13}$ are each a group represented by following Structural Formula (3); and $R^2$, $R^3$, $R^4$, $R^5$, $R^7$, $R^9$, $R^{10}$, $R^{11}$, $R^{12}$ and $R^{14}$ are each hydrogen atom:

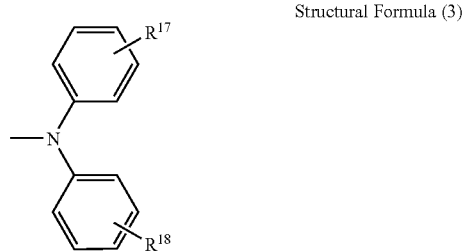

Structural Formula (3)

wherein $R^{17}$ and $R^{18}$ may be the same as or different from each other and each represent one of hydrogen atom, an alkyl group and an aryl group.

3. An organic electroluminescent element according to claim 1, wherein the peropyrene compound is a substituted or unsubstituted 1,3,8,10-tetrakis[N-phenyl-1-naphthylamino]peropyrene, wherein $R^1$, $R^6$, $R^8$ and $R^{13}$ are each a group represented by following Structural Formula (4); and $R^2$, $R^3$, $R^4$, $R^5$, $R^7$, $R^9$, $R^{10}$, $R^{11}$, $R^{12}$ and $R^{14}$ are each hydrogen atom:

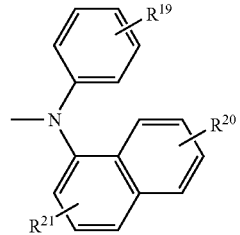

Structural Formula (4)

wherein $R^{19}$, $R^{20}$ and $R^{21}$ may be the same as or different from one another and each represent one of hydrogen atom, an alkyl group and an aryl group.

4. An organic electroluminescent element according to claim 1, wherein the peropyrene compound is a substituted or unsubstituted 1,3,8,10-tetrakis[4,4'-bis(α,α-dimethylbenzyl)diphenylamino]peropyrene, wherein $R^1$, $R^6$, $R^8$ and $R^{13}$ are each a group represented by following Structural Formula (5); and $R^2$, $R^3$, $R^4$, $R^5$, $R^7$, $R^9$, $R^{10}$, $R^{11}$, $R^{12}$ and $R^{14}$ are each hydrogen atom:

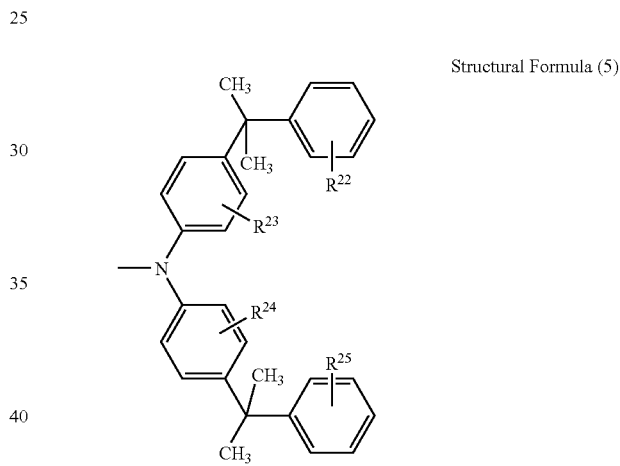

Structural Formula (5)

wherein $R^{22}$, $R^{23}$, $R^{24}$ and $R^{25}$ may be the same as or different from one another and each represent one of hydrogen atom, an alkyl group and an aryl group.

5. An organic electroluminescent element according to claim 1, wherein the thin organic layer has a light-emitting layer, and wherein the light-emitting layer comprises the peropyrene compound as a luminescent material.

6. An organic electroluminescent element according to claim 5, wherein the light-emitting layer is a luminescent-electron-transporting layer, in which the light-emitting layer also serve as the electron-transporting layer.

7. An organic electroluminescent element according to claim 5, wherein the thin organic layer further comprises
a hole-transporting layer, and
an electron-transporting layer,
wherein the light-emitting layer is arranged between the hole-transporting layer and the electron-transporting layer.

8. An organic electroluminescent element according to claim 5, wherein the light-emitting layer comprises a film of the peropyrene compound represented by Structural Formula (1) alone.

9. An organic electroluminescent element according to claim 5, wherein the light-emitting layer further comprises an aromatic amine derivative represented by following Structural Formula (6):

Structural Formula (6)

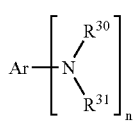

wherein n is an integer of 2 to 4; Ar represents a divalent, trivalent or tetravalent aromatic or heteroaromatic group; and $R^{30}$ and $R^{31}$ may be the same as or different from each other and each represent a monovalent aromatic or heteroaromatic group.

10. An organic electroluminescent element according to claim 9, wherein the aromatic amine derivative is selected from N,N'-dinaphthyl-N,N'-diphenyl-[1,1'-biphenyl]-4,4'-diamine (NPD) represented by following Structural Formula (7) and a derivative thereof.

Structural Formula (7)

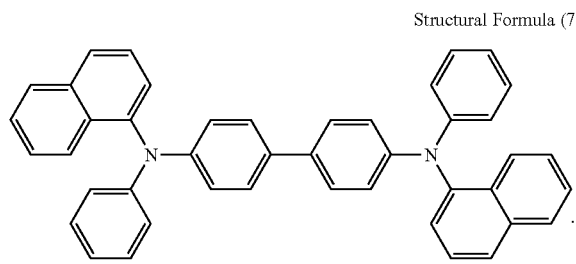

NPD

11. An organic electroluminescent element according to claim 5, wherein the light-emitting layer comprises a carbazole derivative represented by following Structural Formula (8):

Structural Formula (8)

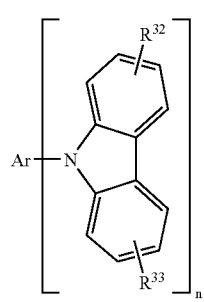

wherein n is an integer of 2 to 4; Ar represents a divalent, trivalent or tetravalent group containing an aromatic ring, or a divalent, trivalent or tetravalent group containing a heteroaromatic ring; $R^{32}$ and $R^{33}$ each independently represent one of hydrogen atom, a halogen atom, an alkyl group, an aralkyl group, an alkenyl group, an aryl group, cyano group, an amino group, an acyl group, an alkoxycarbonyl group, carboxyl group, an alkoxy group, an alkylsulfonyl group, hydroxy group, amido group, an aryloxy group, an aromatic cyclic hydrocarbon group and an aromatic heterocyclic group, each of which may further be substituted with one or more substituents.

12. An organic electroluminescent element according to claim 11, wherein the carbazole derivative is selected from 4,4'-bis(9-carbazolyl)-biphenyl (CBP) represented by following Structural Formula (9) and a derivative thereof:

Structural Formula (9)

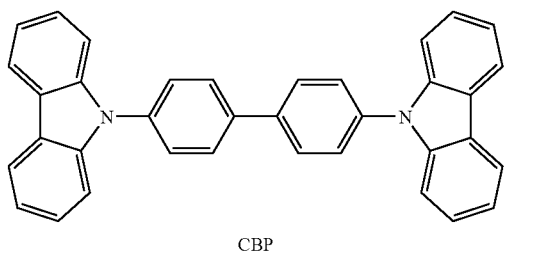

CBP

13. An organic electroluminescent element according to claim 5, wherein the light-emitting layer further comprises a hydroxyquinoline complex represented by following Structural Formula (10):

Structural Formula (10)

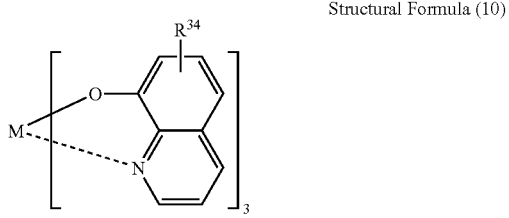

wherein M represents a trivalent metal; and $R^{34}$ represents one of hydrogen atom and an alkyl group.

14. An organic electroluminescent element according to claim 13, wherein the hydroxyquinoline complex is an aluminum hydroxyquinoline complex (Alq) represented by following Structural Formula (11):

Structural Formula (11)

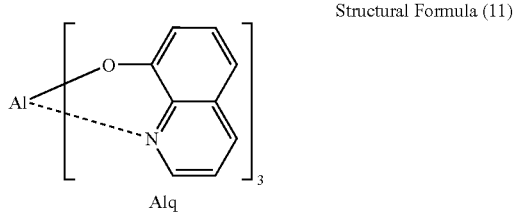

Alq

15. An organic electroluminescent element according to claim 5, wherein the electron-transporting layer comprises, as an electron transporting material, 2,9-dimethyl-4,7-diphenyl-1,10-phenanthroline (BCP) represented by following Structural Formula (17):

Structural Formula (17)

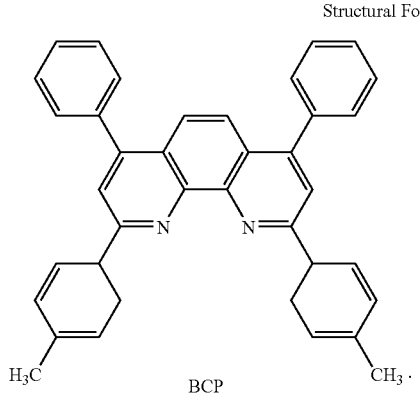

16. An organic electroluminescent element according to claim 1, which is so configured as to emit red light.

17. A peropyrene compound represented by following Structural Formula (1):

Structural Formula (1)

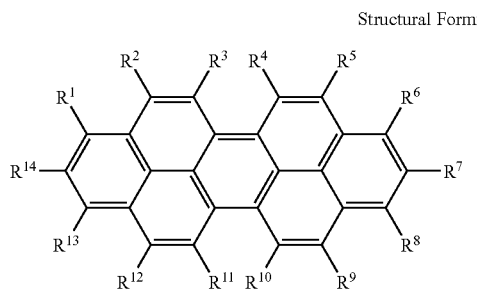

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent hydrogen atom or a substituent:

Structural Formula (2)

wherein $R^{15}$ and $R^{16}$ may be the same as or different from each other and each represent one of hydrogen atom, an alkyl group and an aryl group, where $R^{15}$ and $R^{16}$ may be bound to each other directly or indirectly.

18. A peropyrene compound according to claim 17, which is a substituted or unsubstituted 1,3,8,10-tetrakis(N,N-diphenylamino)peropyrene, wherein $R^1$, $R^6$, $R^8$ and $R^{13}$ are each a group represented by following Structural Formula (3); and $R^2$, $R^3$, $R^4$, $R^5$, $R^7$, $R^9$, $R^{10}$, $R^{11}$, $R^{12}$ and $R^{14}$ are each hydrogen atom:

Structural Formula (3)

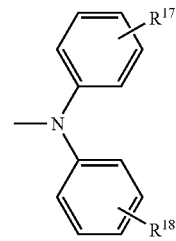

wherein $R^{17}$ and $R^{18}$ may be the same as or different from each other and each represent one of hydrogen atom, an alkyl group and an aryl group.

19. A peropyrene compound according to claim 17, which is a substituted or unsubstituted 1,3,8,10-tetrakis[N-phenyl-1-naphthylamino]peropyrene, wherein $R^1$, $R^6$, $R^8$ and $R^{13}$ are each a group represented by following Structural Formula (4); and $R^2$, $R^3$, $R^4$, $R^5$, $R^7$, $R^9$, $R^{10}$, $R^{11}$, $R^{12}$ and $R^{14}$ are each hydrogen atom:

Structural Formula (4)

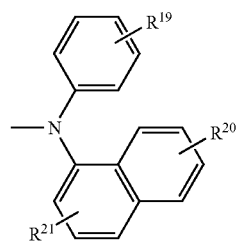

wherein $R^{19}$, $R^{20}$ and $R^{21}$ may be the same as or different from one another and each represent one of hydrogen atom, an alkyl group and an aryl group.

20. A peropyrene compound according to claim 17, which is a substituted or unsubstituted 1,3,8,10-tetrakis[4,4'-bis(α,α-dimethylbenzyl)diphenylamino]peropyrene, wherein $R^1$, $R^6$, $R^8$ and $R^{13}$ are each a group represented by following Structural Formula (5); and $R^2$, $R^3$, $R^4$, $R^5$, $R^7$, $R^9$, $R^{10}$, $R^{11}$, $R^{12}$ and $R^{14}$ are each hydrogen atom:

Structural Formula (5)

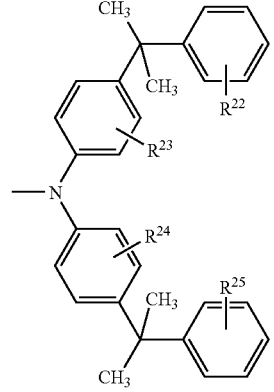

wherein $R^{22}$, $R^{23}$, $R^{24}$ and $R^{25}$ may be the same as or different from one another and each represent one of hydrogen atom, an alkyl group and an aryl group.

21. A peropyrene compound according to claim 17, which is for use as a luminescent material in an organic electroluminescent element.

22. An organic electroluminescent display comprising:
an organic electroluminescent element wherein the organic electroluminescent element comprises
a positive electrode,
a negative electrode, and
a thin organic layer arranged between the positive electrode and the negative electrode,
wherein the thin organic layer comprises, as a luminescent material, a peropyrene compound represented by following Structural Formula (1):

Structural Formula (1)

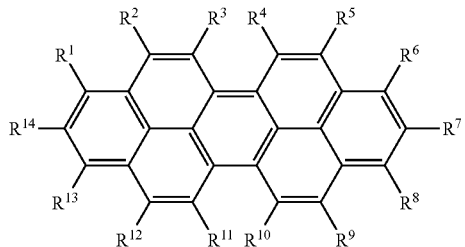

wherein $R^1$, $R^6$, $R^8$ and $R^{13}$ may be the same as or different from one another and each represent a group represented by following Structural Formula (2); and $R^2$, $R^3$, $R^4$, $R^5$, $R^7$, $R^9$, $R^{10}$, $R^{11}$, $R^{12}$ and $R^{14}$ each represent hydrogen atom or a substituent:

Structural Formula (2)

wherein $R^{15}$ and $R^{16}$ may be the same as or different from each other and each represent one of hydrogen atom, an alkyl group and an aryl group, where $R^{15}$ and $R^{16}$ may be bound to each other directly or indirectly.

23. An organic electroluminescent display according to claim 22, which is one of a passive-matrix panel and an active-matrix panel.

* * * * *